US00PP19944P2

(12) United States Plant Patent
Dixon

(10) Patent No.: US PP19,944 P2
(45) Date of Patent: Apr. 21, 2009

(54) ***GAILLARDIA* PLANT NAMED 'TIZZY'**

(50) Latin Name: *Gaillardia×grandiflora*
Varietal Denomination: TIZZY

(76) Inventor: John Dixon, P.O. Box 904, La Conner, WA (US) 98257

( * ) Notice: Subject to any disclaimer, the term of this patent is extended or adjusted under 35 U.S.C. 154(b) by 0 days.

(21) Appl. No.: 12/075,635

(22) Filed: Mar. 12, 2008

(51) Int. Cl.
*A01H 5/00* (2006.01)

(52) U.S. Cl. ..... Plt./431

(58) Field of Classification Search ..... Plt./263, Plt./431

See application file for complete search history.

*Primary Examiner*—S. B McCormick Ewoldt

(57) ABSTRACT

A new cultivar of *Gaillardia* named 'TIZZY' that is distinguishable by compact dwarf habit, medium-green foliage, and large red tubular flowers that bloom in late summer. In combination these traits set 'TIZZY' apart from all other existing varieties of *Gaillardia* known to the inventor.

3 Drawing Sheets

Genus: *GAILLARDIA*.
Species: ×*grandiflora*.
Denomination: 'TIZZY'.

BACKGROUND OF THE INVENTION

The present invention relates to a new and distinct cultivar of blanket flower, an ornamental grown for landscape and container. The new invention is known botanically as *Gaillardia×grandiflora* and will be referred to hereinafter by the cultivar name 'TIZZY'. *Gaillardia* is in the family Asteraceae, under which the commonly referred to "flower" is actually the inflorescence, and made up of smaller ray flowers and disc florets.

The new *Gaillardia* variety named 'TIZZY' is a hybrid seedling selection that resulted from the deliberate cross-pollination between, as female parent, a *Gaillardia* plant which the inventor had raised from seed collected from a plant of *Gaillardia* ×*grandiflora* 'Fanfare' (U.S. Plant Pat. No. 15,892) and, as male parent, a plant which the inventor discovered as a naturally-occurring mutation of *Gaillardia* 'Burgunder' (unpatented). The goal set forth by the inventor was that of producing new *Gaillardia* varieties exhibiting improved flower color, higher petal count, and improved flower form, over all other varieties known to the inventor.

Breeding and selection was conducted by the inventor, at the inventor's nursery located in the state of Washington. The inventor selected 'TIZZY' in 2004 based on the criteria of flower color and plant habit.

The distinguishing characteristics of 'TIZZY' are habit, flower color, flower dimensions, and quantity of flowers.

'TIZZY' is readily distinguishable from the female parent by the color of the ray flowers. The ray flowers of 'TIZZY' are colored red, whereas the ray flowers of the female parent are colored red and yellow.

'TIZZY' is readily distinguishable from the male parent by the shape of the ray flowers. The ray flowers of 'TIZZY' are tubular in shape, whereas the ray flowers of the male parent 'Burgunder' are planar.

The closest comparison plant known to the inventor is the inventor's variety *Gaillardia* 'FRENZY' (U.S. co-pending application 12/075,634). Whereas both 'TIZZY' and 'FRENZY' bear tubular ray flowers, the ray flowers of 'TIZZY' are red in color, whereas the ray flowers of 'FRENZY' are colored red and yellow.

The new *Gaillardia* variety named 'TIZZY' exhibits compact dwarf habit, large red tubular flowers and medium-green foliage. Flowers are fragrant and bloom profusely in late summer. Cultural requirements include full sun and well-draining soil such as loam, given moderate water. Hardiness is classified as USDA Zone 5.

The first asexual reproduction of 'TIZZY' was conducted in 2005 at the inventor's nursery in Washington. The asexual propagation was conducted by the inventor using the method of softwood cuttings. Since that time under careful observation 'TIZZY' has been determined uniform, stable and true to type in subsequent generations of asexual propagation.

SUMMARY OF THE INVENTION

The following traits have been repeatedly observed and represent the distinguishing characteristics of the new *Gallardia* cultivar named 'TIZZY'. These traits in combination distinguish 'TIZZY' from all other existing varieties of *Gaillardia* known to the inventor. 'TIZZY' has not been tested under all possible conditions and phenotypic differences may be observed with variations in environmental, climatic, and cultural conditions, however, without any variance in genotype.

1. 'TIZZY' exhibits compact dwarf habit.
2. 'TIZZY' exhibits medium-green foliage.
3. 'TIZZY' exhibits large red tubular flowers, blooming in late summer.
4. 'TIZZY' grows in full sun and well-draining soil, given moderate water.
5. 'TIZZY' is 40 cm. in height and 47 cm. in width in a 1-litre container.
6. 'TIZZY' is hardy to USDA Zone 5.
7. 'TIZZY' exhibits a large quantity of flowers per inflorescence.

BRIEF DESCRIPTION OF THE DRAWINGS

The accompanying color drawings illustrate the overall appearance of the new *Gaillardia* cultivar named 'TIZZY' showing color as true as is reasonably possible to obtain in color reproductions of this type. Color in the drawings may differ from color values cited in the detailed botanical description, which accurately describe the actual color of the new variety 'TIZZY'. The drawings were made in summer of 6-month-old plants grown under glass then moved to a retractable roof house. The plants are in 1-litre containers and were grown in Washington State.

The drawing labeled

Figure 1:
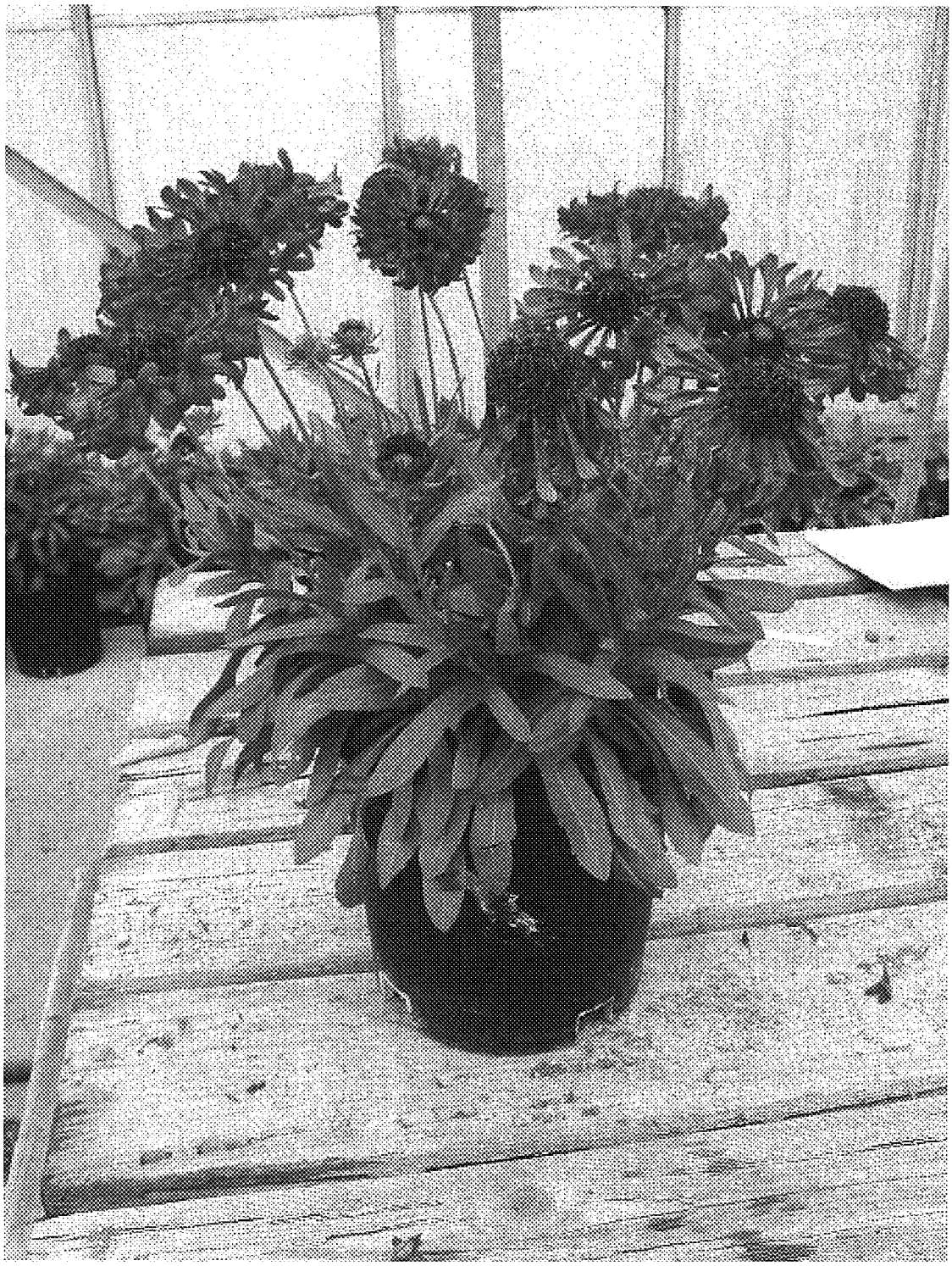
FIG. 1 shows a whole plant of 'TIZZY' with flowers at all stages from bud, through fully expanded, to petal drop.
Figure 2:
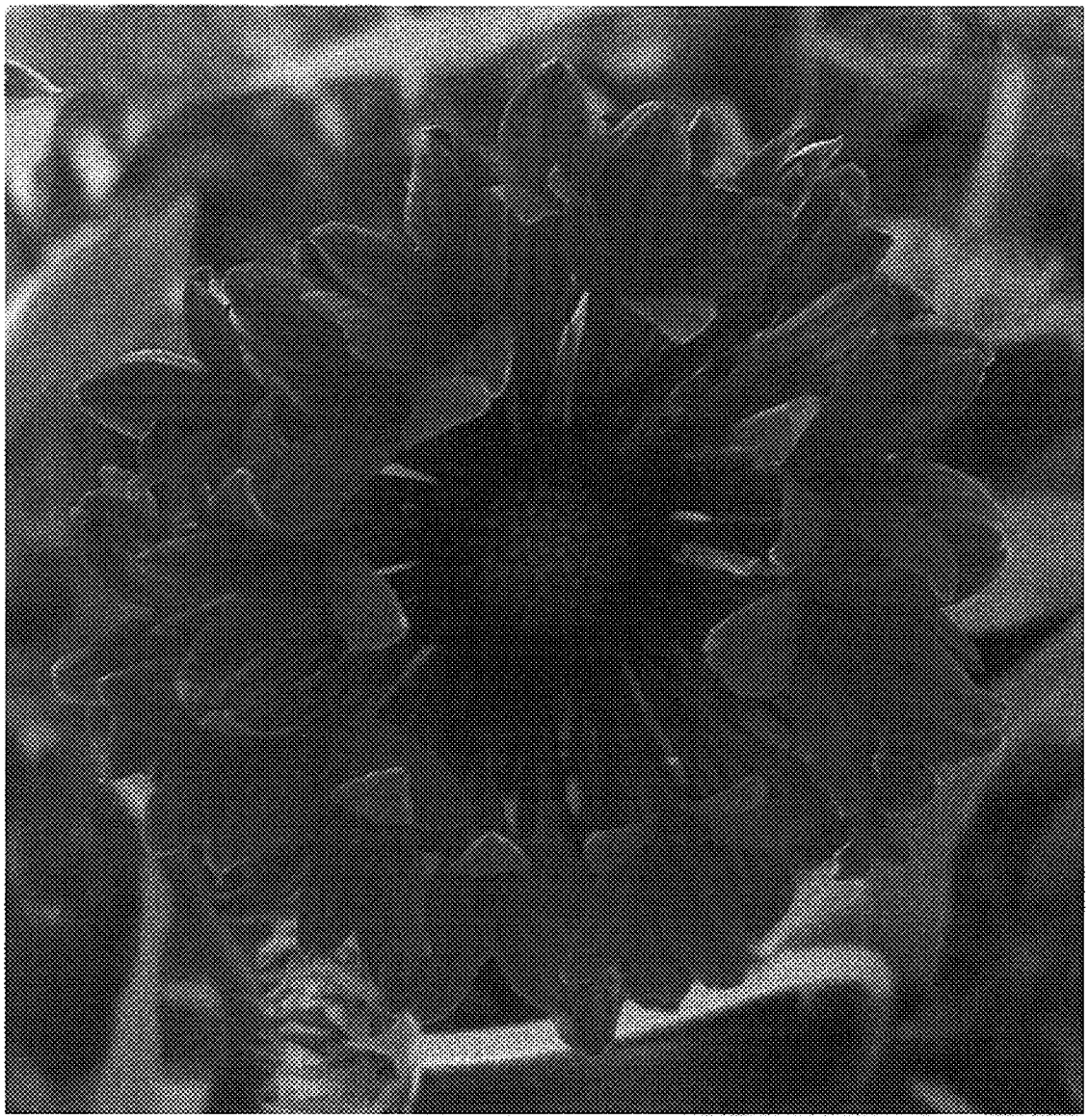

The drawing labeled FIG. 2 exhibits a close up view of a single inflorescence of 'TIZZY' and depicts the uniformly red-colored tubular ray flowers.

Figure 3:
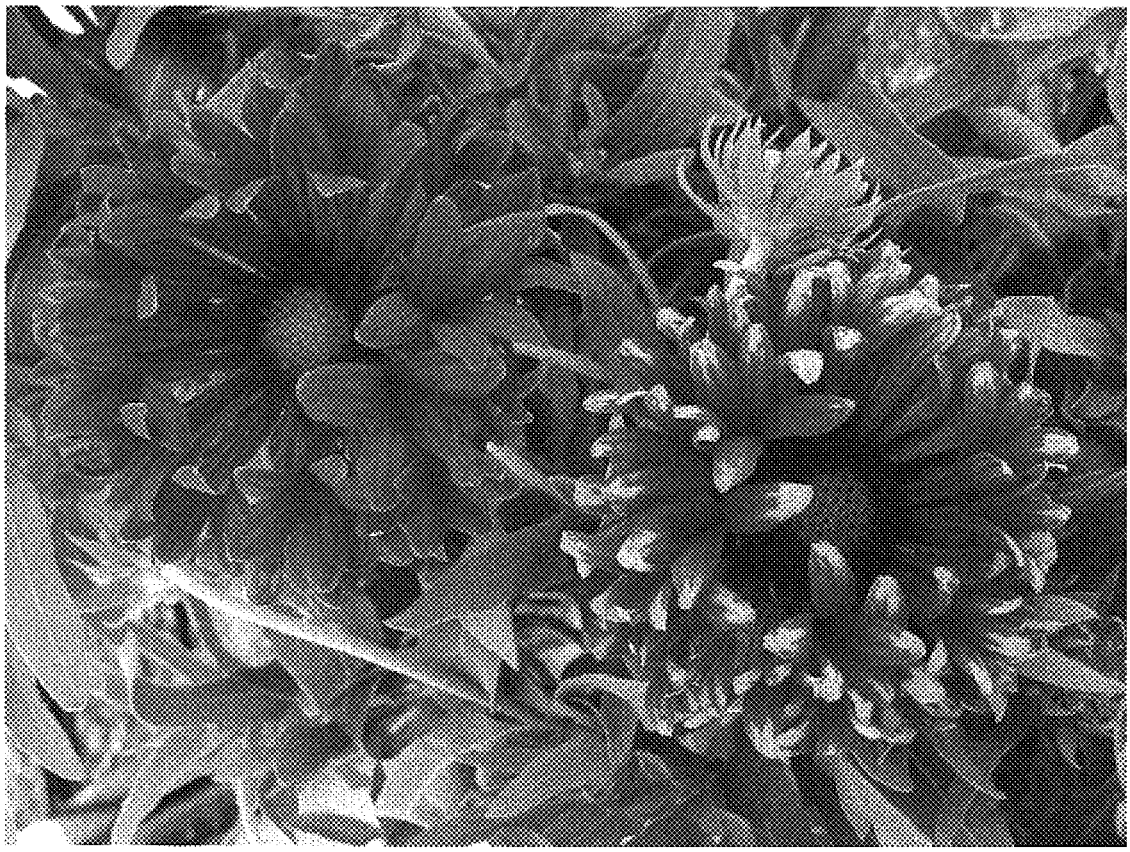

The drawing labeled FIG. 3 depicts and compares the inflorescences of 'TIZZY' (on the left) and the comparison plant *Gaillardia* 'FRENZY' (on the right).

The drawings were made using conventional techniques and although flower and foliage color may appear different from actual color due to light reflectance, it is as accurate as possible by conventional photography.

BOTANICAL DESCRIPTION OF THE PLANT

The following is a detailed botanical description of the new *Gaillardia×grandiflora* cultivar named 'TIZZY'. Observations, measurements, values and comparisons were collected in Arroyo Grande, Calif. during summer, from 6-month-old plants growing out-of-doors in 1-litre containers. Color determinations are made in accordance with The 2001 Royal Horticultural Society Colour Chart from London, England, except where general color terms of ordinary dictionary significance are used.

Botanical classification: *Gaillardia×grandiflora* 'TIZZY'.
Family: Asteraceae.
Genus: *GAILLARDIA.*
Species: *×grandiflora.*
Denomination: 'TIZZY'.
Common name: Blanket flower.
Habit: Dwarf compact habit.
Commercial category: Ornamental.
Use: For landscape or container.
Suggested commercial container size: 1-litre container.
Parentage: *Gaillardia×grandiflora* 'TIZZY' is a hybrid seedling selection resulting from the deliberate cross-pollination of the following parents:
- *Female parent.*—A seedling from *Gaillardia×grandflora* 'Fanfare'.
- *Male parent.*—A single plant mutation of *Gaillardia* 'Burgunder'.

Propagation method: Softwood cuttings.
Rooting system: Fine and fibrous.
Vigor: Moderate.
Time to develop roots (range): 14 to 20 days are needed for an initial cutting to develop roots.
Temperature to develop roots (range): The recommended air temperature is 20–21 Centigrade.
Crop time (range): 1–6 months to produce a 1-litre container from a rooted cutting.
Plant dimensions (1-litre container.): 40 cm. in height and 47 cm. in width.
Cultural requirements: Grow in full sun and well-draining soil such as loam, given moderate water.
Pest or disease resistance: No disease or pest resistance known to the inventor.
Hardiness: USDA Zone 5.
Flowering requirements: 12 hours of light or more is preferred for best flowering.
Stem:
- *Color.*—138C.
- *Dimensions* (*average*).—20 cm. in length and 0.50 cm. in width.
- *Shape.*—Sub-cylindrical.
- *Surface.*—Villous.

Foliage:
- *Type.*—Evergreen.
- *Arrangement.*—Alternate.
- *Internode length* (*average*).—1.50 cm.
- *Division.*—Simple.
- *Margin* (*range*).—Entire to crenate.
- *Shape.*—Spatulate.
- *Dimensions* (*range*).—9 cm to 16 cm. in length and 1 cm. to 3 cm. in width.
- *Apex* (*range*).—Rounded to broadly acute.
- *Base.*—Attenuate.
- *Venation.*—Pinnate.
- *Vein color* (*abaxial and adaxial surfaces*).—147D.
- *Surface* (*abaxial and adaxial*).—*Scaberulose.*
- *Attachment.*—Clasping.
- *Stipules or spines.*—None observed.
- *Leaf color* (*abaxial surface*).—146C.
- *Leaf color* (*adaxial surface*).—146B.
- *Fragrance.*—Resinous scent when bruised.

Inflorescence:
- *Inflorescence type.*—Capitulum.
- *Inflorescence quantity* (*average*).—30 per 1-litre container plant.
- *Aspect.*—Facing upward.
- *Inflorescence diameter.*—9 cm.
- *Inflorescence depth.*—4.50 cm.
- *Inflorescence arrangement.*—Terminal inflorescence.
- *Blooming season.*—Late summer.
- *Peduncle dimensions* (*average*).—13 cm. in length and 0.35 cm. in width.
- *Peduncle shape.*—Cylindrical.
- *Peduncle surface.*—Villous.
- *Peduncle color.*—Ranges between N 138D and 189D.
- *Peduncle strength.*—Strong.
- *Receptacle shape.*—Convex.
- *Receptacle diameter.*—2.75 cm.
- *Receptacle depth.*—0.75 cm.
- *Ray flower.*—Bud color: 53A. Bud surface: Lanate. Bud apex: Rounded. Ray flower shape: Tubular. Ray flower quantity (range): 25–30 per inflorescence. Ray flower color: Ranges between 46B and 46C. Ray flower dimensions: 3.20 cm. in depth and 2.75 cm. in diameter. Ray flower corolla tube width: 0.50 cm. Ray flower surface (ventral surface): Glabrous. Ray flower surface (dorsal surface): Pubescent. Ray flower arrangement: Radiate. Petal quantity: 4 per ray flower. Petals fused or unfused: Midway and basally fused. Petal apex: Rounded. Petal margin: Entire. Petal dimensions: 1 cm. in length and 0.60 cm. in width. Petal color (abaxial and adaxial surfaces): Ranges between 46B and 46C. Sepals: Absent. Reproductive organs: None observed to date. Involucral bract: Quantity (average): 35 per inflorescence. Bract color (abaxial and adaxial surfaces): Ranges between 144A and 146A. Bract length (average): 1.25 cm. Bract width (average): 0.40 cm. Bract apex: Apiculate. Bract base: Truncate. Bract surface (abaxial and adaxial): Villous. Bract shape: Lanceolate. Bract margin. Entire. Disc floret: Disc floret bud color: 14C. Disc floret bud surface: Lanate. Disc floret bud apex: Rounded. Disc floret quantity (range): Approximately 70 per inflorescence. Disc floret dimensions: 12 mm. in depth and 3 mm. in diameter. Disc floret surface (ventral and dorsal): Lanate. Disc floret color: 46A. Reproductive organs: Observed present. Pappus: Pappus quantity (average): 6 per disc floret. Pappus color: 160C. Pappus apex: Caudate. Pappus dimensions: 4 mm. in length and 1 mm. in width. Fragrance of inflorescence: Slightly sweet fragrance. Lastingness of inflorescence (range): 7–14 days, on or off the plant.

Reproductive organs:

*Stamen quantity.*—4.
*Stamen length.*—6 mm.
*Stamen color.*—161A.
*Anther length.*—<1 mm.
*Anther color.*—N186D.
*Anther shape.*—Lanceolate.
*Pollen quantity.*—Heavy.
*Pollen color.*—17A.
*Pistil quantity.*—1.
*Pistil length.*—0.50 cm.
*Stigma dimensions.*—2 mm. in height and 3 mm. in width.
*Stigma form.*—Plumose.
*Stigma shape.*—Forked.
*Stigma color.*—N186D.
*Ovary position.*—Inferior.
*Ovary color.*—150D.
*Ovary shape.*—Globose.
*Ovary dimensions.*—<1 mm. in width and <1 mm. in height.

Fruit:

*Fruit type.*—Cypsela.
*Fruit shape.*—Obpyramidal.

Seed: None observed to date.

What is claimed is:

1. A new and distinct cultivar of *Gaillardia* plant named 'TIZZY' as described and illustrated herein.

* * * * *